United States Patent [19]

Tischlinger

[11] 4,384,406

[45] May 24, 1983

[54] COMBINATION SUTURE CUTTER AND REMOVER

[75] Inventor: Edward A. Tischlinger, Orillia, Canada

[73] Assignee: Cordis Corporation, Miami, Fla.

[21] Appl. No.: 240,971

[22] Filed: Mar. 5, 1981

[51] Int. Cl.³ .............................................. B26B 11/00
[52] U.S. Cl. ........................................ 30/124; 128/305
[58] Field of Search ............ 128/305; 30/124, DIG. 8

[56] References Cited

U.S. PATENT DOCUMENTS

| | | | |
|---|---|---|---|
| 2,556,366 | 6/1951 | Miller | 30/DIG. 8 X |
| 3,624,683 | 11/1971 | Matles | 30/124 |
| 4,098,157 | 7/1978 | Doyle | 128/305 X |
| 4,271,838 | 6/1981 | Lasner et al. | 128/318 |

FOREIGN PATENT DOCUMENTS 1046267  12/1953  France ............................ 128/305

Primary Examiner—Michael H. Thaler
Attorney, Agent, or Firm—Witherspoon & Hargest

[57] ABSTRACT

A combination suture cutting and removing instrument comprising an elongate handle with a head portion extending longitudinally outward from one end thereof. The head portion is curved in a generally crescent configuration with a flat end. A suture cutter blade is positioned across the concave portion of the head and terminates slightly before the flat end which is provided with a "V" shaped notch whereby the flat end may be slipped under the suture to bring the cutter into cutting engagement therewith. After the suture is cut, the "V" shaped notch is positioned around the suture beneath the knot so that upward motion will engage the knot and remove the suture.

6 Claims, 8 Drawing Figures

COMBINATION SUTURE CUTTER AND REMOVER

BACKGROUND AND OBJECTS OF THE INVENTION

This invention relates to a suture cutting and removing instrument and more particularly to a unitary and disposable instrument for both cutting and removing sutures.

The most frequently used method and apparatus for removing sutures comprises first taking a pair of scissors and forcing one of the cutter blades under the exposed suture portion and then cutting same. After this, the suture is pulled out by gripping same with forceps. Obviously, in this procedure two instruments are required. These instruments must be sterile since removal of sutures can leave access where bacteria or the like could enter the patient. Thus said method involves two instruments and sterilizing of same together with the excess handling required for two instruments. It must also be remembered that many patients have great difficulty in even having sutures removed. Consequently any simplification of such procedure is desirable.

In view of the foregoing it is an object of this invention to greatly simplify the method and apparatus employed in removing sutures.

It is another object of this invention to provide a unitary instrument for both cutting and removing sutures.

It is a still further object of this invention to provide a combination suture cutting and removing instrument which is disposable thereby eliminating repeated sterilization problems.

It is yet another object to provide a unitary combination suture cutter and remover capable of substantial time saving in such operation.

Additional objects and advantages will become more apparent when taken in conjunction with the following detailed description and drawings showing by way of example one preferred form of this invention.

IN THE DRAWINGS

FIG. 1 is a side view illustrating the combination device with the cutting blade removed, FIG. 2 is a view similar to FIG. 1 with the cutting blade in position, FIG. 3 is a view similar to FIG. 2 with the snap in retainer installed to retain the cutting blade in position, FIG. 4 is a plan view of the snap in retainer, FIG. 5 is a side view of the snap in retainer, FIG. 6 is a top view of the device of FIG. 1 illustrating the "V" notch in the end of the head portion for engaging the suture knot for suture removal after cutting, FIG. 7 illustrates the use of the combination suture cutter and remover as used in the cutting operation, and FIG. 8 illustrates the manner in which the device is used to remove sutures where the "V" notch is positioned around the suture and under the suture knot for removal of the suture.

DETAILED DESCRIPTION

Figure 1:
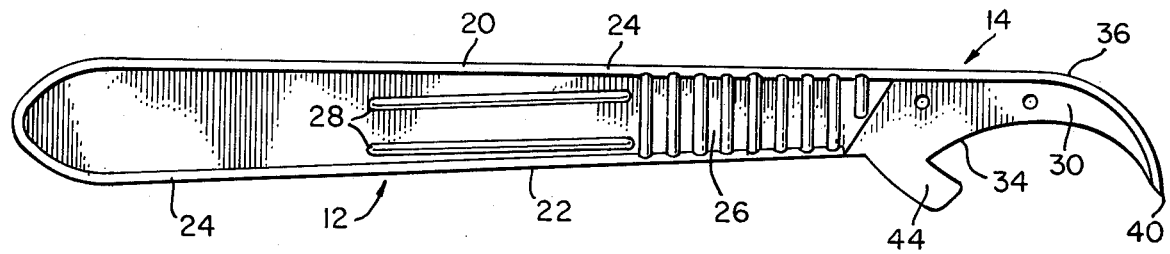
Figure 6:
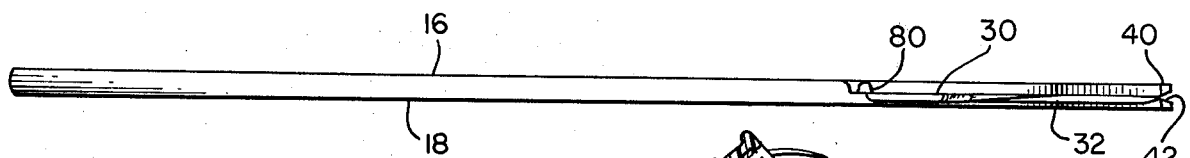

As best illustrated in FIGS. 1 and 6, the device of this invention comprises a handle portion 12 with a head portion 14 extending from one end thereof. The handle is elongate and has vertical sides 16 and 18 connected by a top 20 and a bottom 22. A rounded beading 24 extends around the handle and merges up into the head portion 14. The handle portion 12 is provided with parallel finger gripping elements 26 near the head portion and other gripping members 28 rearwardly and transverse with respect to gripping elements 26.

Head portion 14 extends forwardly from the handle portion and comprises side walls 30 and 32 connected by top and bottom walls 36 and 34. More particularly, the head bottom 34 extends forwardly and gently curves upwardly to its termination while the head top 36 curves forwardly and downwardly and finally meeting the bottom 34 to transversely form the flat head end 40. This head end is provided with a "V" notch 42 for purposes to be described later.

The head portion 14 is also provided with a finger guard 44 which projects outwardly and slightly forward to prevent the user's finger from slipping forward into the blade area.

Figure 2:
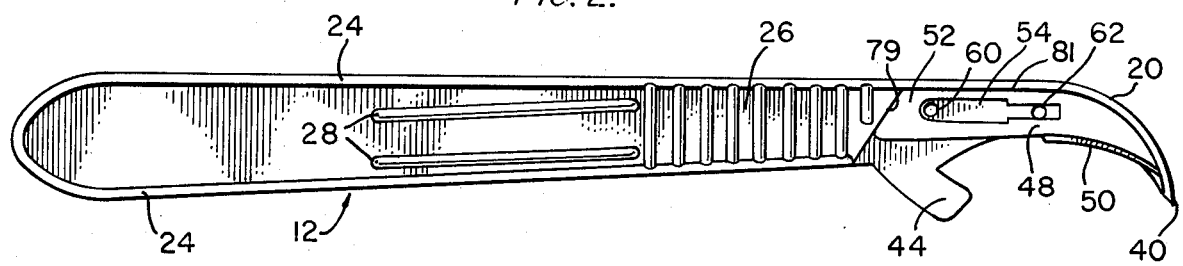

As best illustrated in FIG. 6, side wall 30 of the head portion is generally planar so as to be able to fully accommodate the cutter to be positioned thereon. Referring to FIG. 2, the cutter 48 is positioned on side wall 30. More specifically, the cutter 48 comprises a curved blade portion 50 with a somewhat rectangular holder portion 52 extending rearwardly therefrom. The holder portion 52 is provided with an elongate opening 54 of such size as to clear retainer pin openings 60 and 62 in the head portion 14.

Figure 3:
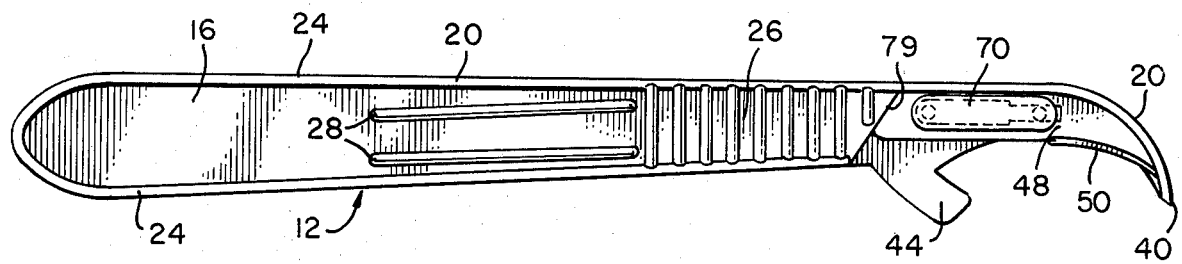
Figure 4:
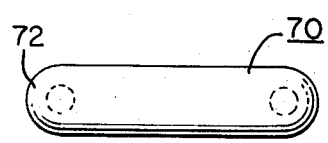
Figure 5:
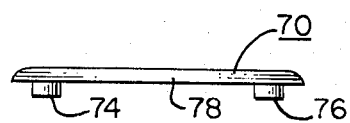

Referring to FIG. 3, the cutter 48 is shown installed on the head portion 14 by means of the snap in retainer 70. As illustrated in FIGS. 4 and 5, the snap in retainer 70 comprises a flat elongated plate 72 having locking pins 74 and 76 projecting outwardly from the bottom face 78. After the cutter 48 is positioned on the head portion 14 as illustrated in FIG. 2, the snap in retainer 70 is snapped into position with locking pin 74 fitting in pin opening 60 and locking pin 76 fitting in opening 62. To further insure that the cutter 48 fits firmly on head side wall 30, the rear wall 79 of the cutter holder 52 is shaped to conform to the shape of the wall 80 of the head portion 14 (see FIGS. 1 and 6). Additionally the bottom configuration 81 of the cutter holder 52 and blade 50 closely conforms to that of the beading 20 to provide a better fit and support.

Figure 7:
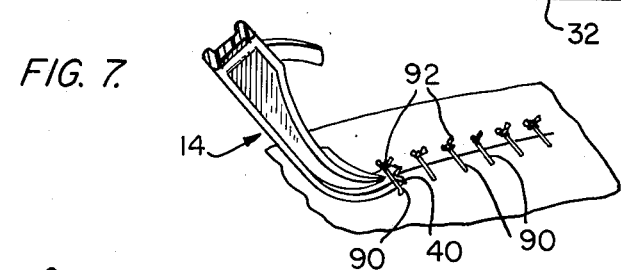
Figure 8:
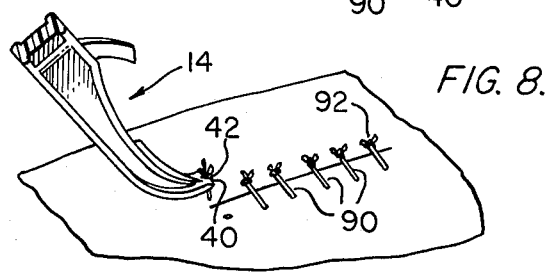

The manner of using the combination suture cutter and remover of this invention is illustrated in FIGS. 7 and 8. Referring first to FIG. 7, the head end 40 is slid under a suture 90 until the cutter blade 50 engages the suture and cuts same. Normally, due to the curvature of the cutter head very little motion is required of the operator.

Referring to FIG. 8, after the suture 90 has been cut, the "V" notch 42 of the head end 40 is positioned below the suture knot 92 in engagement with suture 90 so that upward movement of the head end 40 will result in engagement with the knot 92 and withdrawal of the suture from the patient. Here again the curved shape of the head bottom will assist in removal.

As far as the use of materials for the device of this invention easily molded plastics are quite desirable while the cutter should be made from metal which may be given a rather sharp edge so that very little force is necessary in cutting the sutures. It must also be remembered that all materials must be able to withstand various sterilization procedures as required.

What is claimed is:

1. A combination suture cutting and removing instrument comprising
    a handle portion,
    a head portion extending from said handle portion, said head converging to form an end of reduced size, a notch formed in said head end, and
    a cutter fixedly mounted on the head portion and located completely rearwardly of the notch, said cutter having a cutting blade portion contiguous to the head end whereby in removing sutures the head end may be slid under to the suture so that the cutter blade will engage and sever the suture after which the head end notch is positioned around the suture under the suture knot so that upward movement of the head end will cause the notch portion to engage the knot and remove the suture from the patient.

2. A combination suture cutting and removing instrument comprising
    an elongate handle portion,
    a head portion extending from one end of the handle, said head having a bottom extending forwardly from the handle and curving gently forwardly and upwardly and a top extending from the handle in a forwardly and downwardly curving manner to intersect the bottom and form a transverse flat head end portion,
    a cutter fitted onto the head portion, said cutter having a cutting edge projecting beyond the arcuate edge portion of the head top,
    the head end having a notch formed therein wherein in removing sutures the head end may be gently slid under the suture so that the cutter edge engages the suture to sever same after which the head end notch is positioned around the suture end under the suture knot so that upon upward movement the suture knot is engaged and the suture is removed from the patient, said cutter located completely rearwardly of the notch.

3. The invention as set forth in claim 2 and wherein the instrument is provided with a finger guard to protect the user from the cutter's cutting edge.

4. The invention as set forth in claim 3 and wherein the cutter is held in position on the head portion by means of a snap in retainer.

5. The invention as set forth in claim 4 and wherein the handle portion and the head portion are integral and made of the same material.

6. A combination suture cutting and removing instrument comprising
    an elongate generally flat handle portion having parallel vertical sides connected by a top and bottom and wherein the vertical sides are of substantial greater height than the top and bottom are wide,
    a head portion extending from one end of the handle as an extension thereof with parallel sides and a top and a bottom, said bottom extending forwardly from the end of the handle bottom and gently curving upwardly to its termination, the top curving forwardly and downwardly and finally meeting the bottom to transversely form a thin head end,
    a cutter fitted in the head portion, said cutter having a cutting edge generally spanning the arc formed by the curved top of the head portion, and
    the head end having a "V" notch formed therein wherein in removing sutures the head end may be slid under the suture until the cutter edge engages and cuts same whereupon the "V" notch is placed below the suture knot riding on the suture so that upward movement will cause the head end to raise and remove the suture from the patient, said cutter located completely rearwardly of the notch.

* * * * *